United States Patent
Kennedy

(10) Patent No.: US 8,009,040 B2
(45) Date of Patent: Aug. 30, 2011

(54) MEDICATION DISPENSING SYSTEM

(76) Inventor: Philip R. Kennedy, Duluth, GA (US)

( * ) Notice: Subject to any disclaimer, the term of this patent is extended or adjusted under 35 U.S.C. 154(b) by 316 days.

(21) Appl. No.: 12/474,401

(22) Filed: May 29, 2009

(65) Prior Publication Data

US 2009/0295575 A1 Dec. 3, 2009

Related U.S. Application Data

(60) Provisional application No. 61/057,308, filed on May 30, 2008.

(51) Int. Cl.
*G08B 21/00* (2006.01)
(52) U.S. Cl. ....................................................... 340/540
(58) Field of Classification Search ............... 340/573.1, 340/309.16, 825.36, 384.5, 539.12, 540; 700/231, 236, 240
See application file for complete search history.

(56) References Cited

U.S. PATENT DOCUMENTS

| | | | |
|---|---|---|---|
| 5,390,238 A | 2/1995 | Kirk et al. | |
| 5,752,621 A | 5/1998 | Passamante | |
| 6,004,020 A | 12/1999 | Bartur | |
| 6,150,942 A | 11/2000 | O'Brien | |
| 6,263,259 B1 | 7/2001 | Bartur | |
| 6,988,634 B2 | 1/2006 | Varis | |
| 7,006,893 B2 | 2/2006 | Hart et al. | |
| 7,048,141 B2 | 5/2006 | Abdulhay et al. | |
| 7,154,397 B2 | 12/2006 | Zerhusen et al. | |
| 7,213,721 B2 | 5/2007 | Abdulhay et al. | |
| 7,440,817 B2 | 10/2008 | Fu | |
| 7,502,664 B2 | 3/2009 | Berg | |
| 7,502,666 B2 | 3/2009 | Siegel et al. | |
| 7,515,988 B1 | 4/2009 | Frederick et al. | |
| 2001/0028308 A1 | 10/2001 | De La Huerga | |
| 2002/0032582 A1 | 3/2002 | Feeney, Jr. et al. | |
| 2003/0222090 A1 | 12/2003 | Abdulhay et al. | |
| 2006/0201961 A1* | 9/2006 | Abdulhay et al. | 221/9 |
| 2007/0093935 A1* | 4/2007 | Fu | 700/237 |
| 2007/0257051 A1* | 11/2007 | Abdulhay et al. | 221/2 |
| 2008/0080319 A1* | 4/2008 | Niemiec et al. | 368/10 |
| 2008/0173711 A1* | 7/2008 | Handfield et al. | 235/385 |

FOREIGN PATENT DOCUMENTS

| | | |
|---|---|---|
| JP | 2004287956 A | 10/2004 |
| JP | 2005204685 A | 8/2005 |
| JP | 2007014463 A | 1/2007 |
| JP | 2009100855 A | 5/2009 |

OTHER PUBLICATIONS

WIPO, "Notification of Transmittal of the International Search Report and the Written Opinion of the International Searching Authority" (PCT/ISA/220, 210, 237); Nov. 2, 2011.

* cited by examiner

*Primary Examiner* — Phung Nguyen
(74) *Attorney, Agent, or Firm* — Bryan W. Bockhop; Bockhop & Associates, LLC

(57) ABSTRACT

A device for dispensing medication includes a medication hopper, a dispensing mechanism that is configured to dispense medication from the hopper to a user and a processor. The processor is in communication with a communication network and is configured to generate instructions to the dispensing mechanism that cause the dispensing mechanism to dispense medications according to a stored prescription and track an amount of medication in the medication hopper. If the amount is less than a predetermined threshold, then the processor is configured to send a message to a designated entity indicating that the amount of medication in the hopper is less than the threshold.

11 Claims, 2 Drawing Sheets

MEDICATION DISPENSING SYSTEM

CROSS-REFERENCE TO RELATED APPLICATION(S)

This application claims the benefit of U.S. Provisional Patent Application Ser. No. 61/057,308, filed May 30, 2008, the entirety of which is hereby incorporated herein by reference.

BACKGROUND OF THE INVENTION

1. Field of the Invention

The present invention relates to medication dispensing systems and, more specifically, to a system for tracking administration of medications to patients.

2. Description of the Prior Art

Certain patients have difficulty complying with medication prescriptions issued by their physicians. For example, some geriatric patients having certain neurological pathologies may forget when to take their medications and the quantities they are to take. They may also forget to reorder their medications when the get low, which can result in their not having the medication when needed.

Therefore, there is a need for a device and method that automates the dispensing, tracking and reordering of medications.

SUMMARY OF THE INVENTION

The disadvantages of the prior art are overcome by the present invention which, in one aspect, is a medication dispensing system that include at least one medication storage hopper configured to store a medication therein. A medication dispensing mechanism is configured to dispense an amount of the medication specified by a medication prescription to a predetermined location at a time specified by the medication prescription in a response to a dispensing instruction signal. A user interface includes a patient notification mechanism. A processor, in communication with a global computer network, is configured to: store the medication prescription; issue the dispensing instruction signal to the medication dispensing mechanism at the time specified by the medication prescription, wherein the dispensing instruction signal instructs the medication dispensing mechanism to dispense the amount of the medication specified by the medication prescription; cause the patient notification mechanism to issue an alert once the amount of the medication has been dispensed to the predetermined location; maintain a count of how many units of the medication are stored in the hopper; and notify a remote computer when the count indicates that fewer than a predetermined number of units of the medication remain in the hopper.

In another aspect, the invention is a system for dispensing at a medication that includes a medication storage hopper configured to store the medication therein. A medication dispensing mechanism is configured to dispense an amount of the medication specified by a medication prescription to a predetermined location at a time specified by the medication prescription in a response to a dispensing instruction signal. A user interface that includes a patient notification mechanism that is configured to issue a audible alarm; a keyboard by which the medication prescription is entered to the processor; and a mechanism for a patient to acknowledge receipt of the amount of medication that has been dispensed. A processor that is in communication with a global computer network is configured to: store the medication prescription; issue the dispensing instruction signal to the medication dispensing mechanism at the time specified by the medication prescription, wherein the dispensing instruction signal instructs the medication dispensing mechanism to dispense the amount of the medication specified by the medication prescription; cause the patient notification mechanism to sound the audible alarm once the amount of the medication has been dispensed to the predetermined location and cause the notification mechanism to cease sounding the alarm when the patient has acknowledged receipt of the amount of medication that has been dispensed; maintain a count of how many units of the medication are stored in the hopper; notify a remote computer via the global computer network when the count indicates that fewer than a predetermined number of units of the medication remain in the hopper; send a signal via the global computer network to an individual other than the patient when the patient has failed to acknowledge receipt of the amount of medication within a predetermined amount of time after the alert has been issued by the patient notification mechanism; and receive from a remote computer, via the global computer network, an instruction to change the prescription, thereby causing the processor to store a changed prescription in response thereto.

In yet another aspect, the invention is a method of dispensing a medication employing a computer processor-controlled medication dispensing system that is coupled to a global computer network. A medication prescription is stored in a computer readable memory. An amount of the medication specified in the medication prescription is stored in a hopper and the amount is added to a number stored in a predetermined location of the computer readable memory. The number corresponds to a total amount of medication stored in the hopper. The computer processor periodically determines if a medication dispensing event time specified by the medication prescription has been reached. When the medication dispensing event time specified by the medication prescription has been reached, a signal is sent from the computer processor to an automatic medication dispensing mechanism to dispense a prescribed amount of medication from the hopper to a predetermined location. A signal is also sent from the computer processor to a sound interface that causes the sound interface to sound an audible alarm indicating that the medication is ready to be taken. The computer processor subtracts the prescribed amount from the number corresponding to the total amount of medication stored in the hopper and stores the result in the predetermined location of the computer readable memory. The number stored in the predetermined location of the computer readable memory is compared to a threshold number. If the number stored in the predetermined location of the computer readable memory is not greater than the threshold number then a low medication signal is sent from the computer processor to a remote computer via the global computer network indicating that the hopper is running out of the medication.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Figure 1:
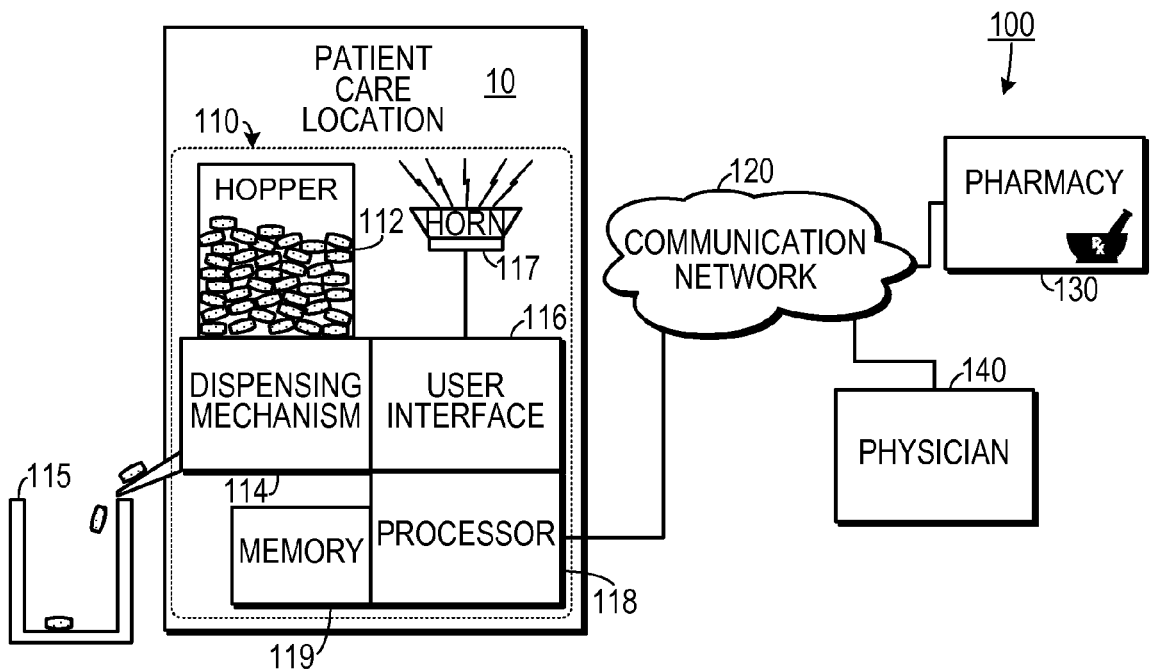
FIG. 1 is a schematic diagram of one embodiment of a medication dispensing system.

A preferred embodiment of the invention is now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Also, as used herein, "global computer network" includes the Internet.

In one embodiment, the invention is a device for dispensing medication that includes a medication hopper, a dispensing mechanism that is configured to dispense medication from the hopper to a user and a processor. The processor is in communication with a communication network and is configured to generate instructions to the dispensing mechanism that cause the dispensing mechanism to dispense medications according to a stored prescription. The processor also tracks an amount of medication in the medication hopper. If the amount is less than a predetermined threshold, then the processor is configured to send a message to a designated entity indicating that the amount of medication in the hopper is less than the threshold.

As shown in FIG. 1, one embodiment is a medication dispensing system 100 that integrates an automatic medication dispenser 110 with a pharmacy 130 and a physician 140 via a communication network 120 such as a telephone network or a global computer network (or other computer network in certain embodiments). The automatic medication dispenser 110 includes a medication hopper 112 (more than one hopper may be employed in embodiments configured to dispense more than one kind of medication) that supplies medication to a dispensing mechanism 114, from which the patient or the patient's caregiver receives the medication in the prescribed amount at the prescribed time.

The dispensing mechanism 114 is responsive to a processor 118 (which includes a computer memory 119), which issues dispensing instructions according to a prescription entered into the processor 118 via a user interface 116 (such as a keypad or a touch screen). Alternately, the prescription may be transmitted directly from the physician 140 to the processor 118 via the communication network 120. When the processor 118 issues a dispensing instruction, the dispensing mechanism 114 dispenses the exact amount of medication indicated by the processor 118 at the indicated time to a predetermined location 115 such as a medication cup. Each time the medication is dispensed, the processor 118 tracks the amount dispensed and the amount remaining in the hopper 112. Once the amount in the hopper 112 falls below a threshold, the pharmacy 130 is alerted via the communication network 120 and the medication is re-ordered, if refills are allowed under the prescription. If the prescription is expired, the physician 140 may be alerted. The system may also provide information regarding compliance and other data to the physician 140.

The system may also generate a notification (such as an audible alarm 117 or a flashing light) when it is time to dispense the medication to assist the patient in remembering to take the medication. The system could also provide such notification by sending a message to the patient's cell phone or the caregiver's cell phone. The system could also employ an alarm system that the patient wears to send a reminder.

When a prescription refill is added to the hopper 112, the amount added is entered into the processor 118 via the user interface 116. The processor 118 adds this amount to a counter that tracks the amount of the medication in the hopper 112. The system could employ several different hoppers, each corresponding to a different medication. In one embodiment, the system includes a reader (such as a bar code reader) that reads the prescription number from the label so that a medication is dispensed into the correct hopper. A text reader could also be employed to achieve this function.

Figure 2:
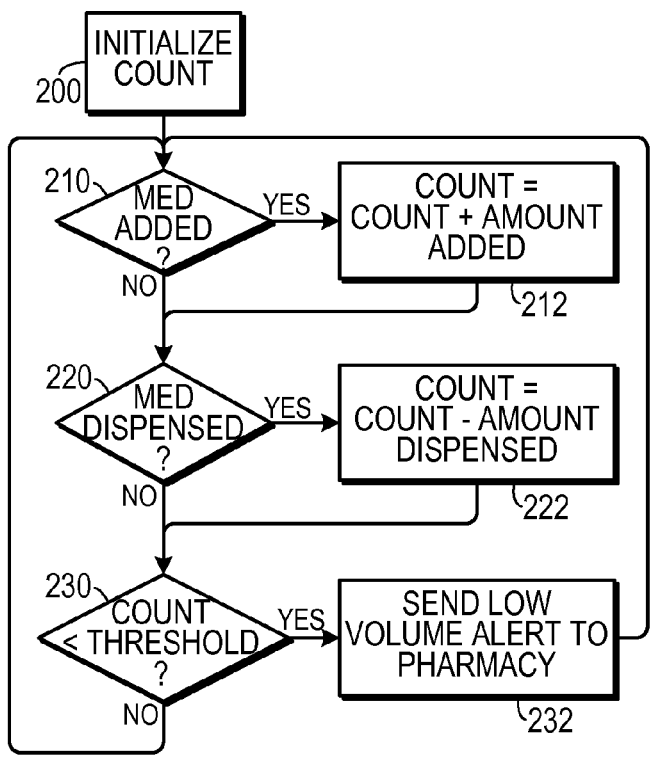
FIG. 2 is a flow chart showing one embodiment of actions executed by the medication dispensing system shown in FIG. 1.

As shown in FIG. 2, in one method of tracking medications employing the system shown in FIG. 1, a medication quantity counter is initialized 200 to a default value (such as zero). If medication is added 210 (i.e., either when the first amount of medication is added or when the prescription is refilled), the system adds 212 the amount of medication added to the medication quantity counter. When medication is dispensed 220, the system subtracts 222 the amount dispensed from the medication quantity counter. If the amount of the medication quantity counter is less than a predetermined threshold 230, then the system sends a low volume alert to the pharmacy 232 indicating that it is time to refill the prescription. The pharmacy may then either mail the refill to the patient or send a technician to reload the hopper with the refill. Similarly, the patient or the caregiver could pick up the refill.

Figure 3:
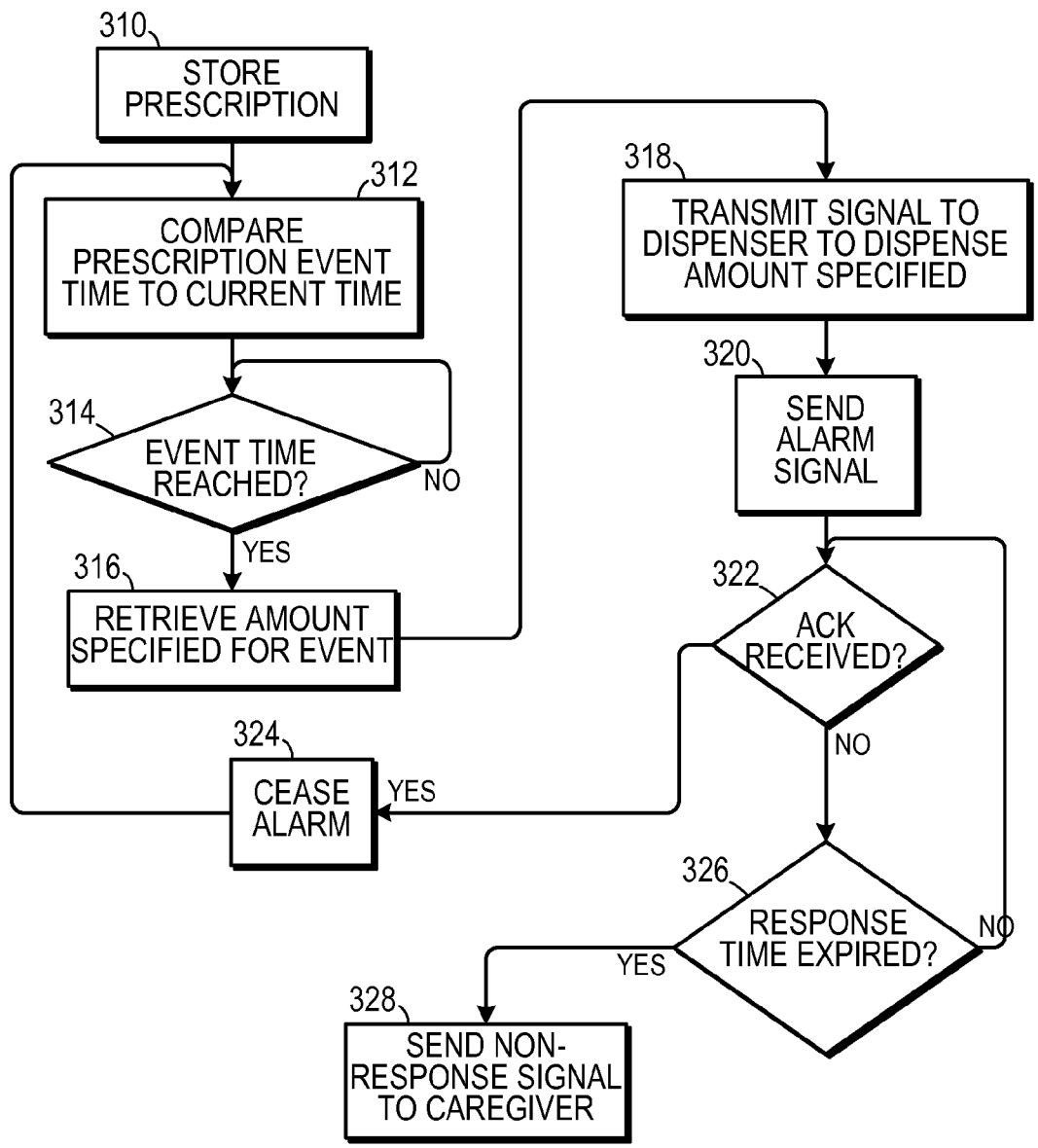
FIG. 3 is a flow chart showing one embodiment of a dispensing procedure.

The system ensures that medications are dispensed according to schedule and that refills are delivered to the patient in a timely manner. As shown in FIG. 3, in one embodiment, the processor is programmed to execute the following steps. When a new prescription is issued, the prescription is stored 310 by the processor in the memory. The prescription may include such information as: the number of pills or capsules that are currently being added to the hopper, the times at which the medication is to be dispensed and taken by the patient and the amount of the medication that is to be dispensed at each time. Periodically, the processor compares 312 the current time to a prescription event time (i.e., at time at which the medication is to be taken by the patient) and, if the event time has been reached 314, then the processor determines the number of pills or capsules that are to be dispensed at that event time. The processor then instructs 318 the dispenser to dispense the amount of medication specified in the prescription and also causes an alarm to be sounded 320 to indicate to the patient that it is time to take the medication.

The processor also determines 322 whether the patient has acknowledged receipt of the medication. If the patient's acknowledgement has been received, then the processor causes the alarm to cease sounding 324. On the other hand, if the acknowledgement has not been received, then the system determines 326 if a predetermined response time has expired and, if it has expired, then the processor sends a signal 328 via the global computer network to a remote computer that indicates to a caregiver (such as a nurse, a relative or a physician) that the patient has not acknowledged receipt of the medication. The signal could then be displayed on the remote computer, or it could be forwarded to the caregiver in the form of a page or a wireless telephone message.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A medication dispensing system, comprising:
   a. at least one medication storage hopper configured to store a medication therein;
   b. a medication dispensing mechanism, configured to dispense an amount of the medication specified by a medication prescription to a predetermined location at a time specified by the medication prescription in a response to a dispensing instruction signal;
   c. a user interface that includes a patient notification mechanism and
   d. a processor, in communication with a global computer network, that is configured to:
      i. store the medication prescription;
      ii. issue the dispensing instruction signal to the medication dispensing mechanism at the time specified by the medication prescription, wherein the dispensing instruction signal instructs the medication dispensing mechanism to dispense the amount of the medication specified by the medication prescription;
      iii. cause the patient notification mechanism to issue an alert once the amount of the medication has been dispensed to the predetermined location;
      iv. maintain a count of how many units of the medication are stored in the hopper; and
      v. notify a remote computer when the count indicates that fewer than a predetermined number of units of the medication remain in the hopper;
   wherein the user interface includes a mechanism for a patient to acknowledge receipt of the amount of medication that has been dispensed and wherein the processor causes the notification mechanism to cease the alert when the patient has acknowledged receipt of the amount of medication that has been dispensed; and wherein the processor is further configured to send a signal via the global computer network to an individual other than the patient when the patient has failed to acknowledge receipt of the amount of medication within a predetermined amount of time after the alert has been issued by the patient notification mechanism.

2. The medication dispensing system of claim 1, wherein the user interface comprises a keyboard by which the medication prescription is entered to the processor.

3. The medication dispensing system of claim 1, wherein the patient notification mechanism includes an audible alarm.

4. The medication dispensing system of claim 1, wherein the processor is further configured to receive from a remote computer, via the global computer network, an instruction to change the prescription, thereby causing the processor to store a changed prescription in response thereto.

5. A system for dispensing at a medication, comprising:
   a. a medication storage hopper configured to store the medication therein;
   b. a medication dispensing mechanism, configured to dispense an amount of the medication specified by a medication prescription to a predetermined location at a time specified by the medication prescription in a response to a dispensing instruction signal;
   c. a user interface that includes:
      i. a patient notification mechanism that is configured to issue a audible alarm;
      ii. a keyboard by which the medication prescription is entered to the processor; and
      iii. a mechanism for a patient to acknowledge receipt of the amount of medication that has been dispensed; and
   d. a processor, in communication with a global computer network, that is configured to:
      i. store the medication prescription;
      ii. issue the dispensing instruction signal to the medication dispensing mechanism at the time specified by the medication prescription, wherein the dispensing instruction signal instructs the medication dispensing mechanism to dispense the amount of the medication specified by the medication prescription;
      iii. cause the patient notification mechanism to sound the audible alarm once the amount of the medication has been dispensed to the predetermined location and cause the notification mechanism to cease sounding the alarm when the patient has acknowledged receipt of the amount of medication that has been dispensed;
      iv. maintain a count of how many units of the medication are stored in the hopper;
      v. notify a remote computer via the global computer network when the count indicates that fewer than a predetermined number of units of the medication remain in the hopper;
      vi. send a signal via the global computer network to an individual other than the patient when the patient has failed to acknowledge receipt of the amount of medication within a predetermined amount of time after the alert has been issued by the patient notification mechanism; and
      vii. receive from a remote computer, via the global computer network, an instruction to change the prescription, thereby causing the processor to store a changed prescription in response thereto.

6. The system of claim 5, wherein the signal sent to the individual other than the patient comprises a remote electronic device to indicate to a care giver that the patient has not acknowledged receipt of the medication.

7. A method of dispensing a medication employing a computer processor-controlled medication dispensing system that is coupled to a global computer network, comprising the actions of:
   a. storing a medication prescription in a computer readable memory;
   b. storing an amount of the medication specified in the medication prescription in at least one hopper and adding the amount to a number stored in a predetermined location of the computer readable memory, the number corresponding to a total amount of medication stored in the hopper;
   c. periodically determining, using the computer processor, when a medication dispensing event time specified by the medication prescription has been reached;
   d. when the medication dispensing event time specified by the medication prescription has been reached, sending a signal from the computer processor to an automatic medication dispensing mechanism to dispense a prescribed amount of medication from the hopper to a predetermined location and then sending a signal from the computer processor to a sound interface that causes the sound interface to sound an audible alarm indicating that the medication is ready to be taken;
   e. employing the computer processor to subtract the prescribed amount from the number corresponding to the total amount of medication stored in the hopper and storing the result in the predetermined location of the computer readable memory;

f. comparing the number stored in the predetermined location of the computer readable memory to a threshold number and, if the number stored in the predetermined location of the computer readable memory is not greater than the threshold number then sending a low medication signal from the computer processor to a remote computer via the global computer network indicating that the hopper is running out of the medication;

g. determining, with the computer processor, if an acknowledgement has been input to a user interface acknowledging receipt of prescribed amount of medication dispensed from the dispensing mechanism within a predetermined amount of time after the step of sending a signal from the computer processor to an automatic medication dispensing mechanism to dispense a prescribed amount of medication from the hopper to a predetermined location;

h. if the acknowledgement has been input to the user interface within the predetermined amount of time, then causing the audible alarm to cease sounding; and i. if the acknowledgement has not been input to the user interface within the predetermined amount of time, then causing a message to be sent from the computer processor to a remote computer via the global computer network notifying the remote computer that the patient has failed to acknowledge receipt of the medication.

8. The method of claim 7, wherein the remote computer comprises a computer at a pharmacy.

9. The method of claim 7, wherein the remote computer comprises a computer maintained by a caregiver.

10. The method of claim 7, wherein the remote computer comprises a computer maintained by a physician.

11. The method of claim 7, wherein the remote computer, upon receipt of the message, sends a message to a caregiver over a wireless network indicating that the patient has not acknowledged receipt of the medication.

* * * * *